United States Patent [19]

Chosnek et al.

[11] Patent Number: 5,136,083

[45] Date of Patent: Aug. 4, 1992

[54] PROCESS FOR THE PURIFICATION OF 4-ACETOXYSTYRENE

[75] Inventors: Jack Chosnek, Corpus Christi; George E. Beck, Portland, both of Tex.; Donna L. Keene, Carrollton, Va.; Siegbert Rittner, Mörfelden-Walldorf; Volker Hautzel, Flörsheim, both of Fed. Rep. of Germany

[73] Assignee: Hoechst Celanese Corporation, Somerville, N.J.

[21] Appl. No.: 575,513

[22] Filed: Aug. 30, 1990

[51] Int. Cl.$^5$ ............... C07C 67/48; C07C 67/52
[52] U.S. Cl. ............... 560/130; 526/319; 568/813
[58] Field of Search ........................ 560/130

[56] References Cited

U.S. PATENT DOCUMENTS 3,621,664 11/1971 Saxer .................... 62/88
4,927,956 5/1990 Vicari et al. .............. 560/130

OTHER PUBLICATIONS

Winnacker-Kuchler, *Chemische Technologie* (*Chemical Technology*), 4th Edition, vol. 6, (1982), p. 148.

*Chem.-Ing.-Techn.* 57, (1985), No. 2, pp. 91-102.

*Primary Examiner*—Jose G. Dees
*Assistant Examiner*—Vera C. Clarke
*Attorney, Agent, or Firm*—Donald R. Cassady

[57] ABSTRACT

The present invention relates to a process for the purification of 4-acetoxystyrene from a crude product mixture comprising 4-acetoxystyrene and typically 5 or more contaminants in substantial amount.

The crude product mixture is purified by melt crystallization by cooling the mixture to a temperature ranging from about +8° C. to about −50° C., whereby at least a first portion of the mixture is crystallized; removing the liquid remaining from contact with the crystallized first portion of the mixture; and, subsequently slowly heating the crystallized first portion, while simultaneously removing liquid which forms due to the heating, whereby impurities contained in the liquid which forms are removed from the crystallized first portion.

Surprisingly, despite the large number of contaminants present, and use of the process to purify crude product mixtures containing as little as 50% by weight 4-acetoxystyrene, purities as high as 99.9% by weight have been obtained using multiple melt-crystallization steps of the process of the invention.

24 Claims, No Drawings

PROCESS FOR THE PURIFICATION OF 4-ACETOXYSTYRENE

BACKGROUND OF THE INVENTION

1. Field of the Invention

The present invention pertains to a method for the purification of 4-acetoxystyrene. In particular, the method comprises at least one crystallization without the aid of a solvent.

2. Background of the Invention

The product 4-acetoxystyrene, which is typically obtained through the elimination of water from 4-acetoxyphenylmethyl carbinol, represents an important intermediate from which a variety of compounds are produced. The 4-acetoxystyrene is used as a monomer for the manufacture of poly(4-acetoxystyrene) from which poly(4-hydroxystyrene) and various copolymers are produced. In addition, 4-acetoxystyrene can be used to prepare 4-hydroxystyrene from which numerous derivatives having medical applications are produced. Polymers and copolymers of the kind described above are applied, for example, in the electronic industry as a binder in photoresists, in adhesives to improve their temperature stability, and in the surface treatment of metals, for the replacement of toxic chromate as a subcoating on the metals. The poly(4-hydroxystyrene) polymers and copolymers are also used as a UV absorber and flame-retardant additive that cannot be extracted from the plastic and as an additive in other polymers such as polyesters, nylon, polyurethanes, etc. in order to substantially improve their adhesive properties to glass and mineral fillers.

According to the state of the art, 4-acetoxystyrene, which is normally contaminated by starting reaction components such as 4-acetoxyphenylmethyl carbinol as well as by other compounds such as, but not limited to, acetic acid, ethyl benzene, 1-phenyl ethanol, 4-ethyl phenol, 4-hydroxystyrene, 4-ethylphenyl acetate, 4-acetoxyacetophenone, 1-(4-acetoxyphenyl)-ethane, heavy ends and water, has typically been purified by rectification. Since, interalia, the rectification is carried out at reduced pressure, the boiling temperatures of 4-acetoxystyrene and impurities such as 4-hydroxystyrene and 4-ethylphenyl acetate lie close together. Thus, a large number of separating stages are required, which subjects the mixture of reactants to high thermal stress. This is particularly a problem, since both 4-acetoxystyrene and the 4-acetoxyphenylmethyl carbinol reactant possess only limited thermal stability. As a result, a considerable amount of the 4-acetoxystyrene and the 4-acetoxyphenylmethyl carbinol are destroyed during rectification by subsequent reactions such as resinification, the formation of oligomers and also by polycondensation and polymerization. The process yield for conversion of 4-acetoxyphenylmethyl carbinol to 4-acetoxystyrene is reduced accordingly. In addition, this limited thermal stability also prevents the recycle of unconverted 4-acetoxyphenylmethyl carbinol, again reducing the potential yield of the process.

It was, therefore, the object of the present invention to provide a process for the preparation of pure 4-acetoxystyrene from crude mixtures, which process works under low thermal stress conditions and provides a high efficiency separation, leading to good yields of 4-acetoxystyrene having high purity.

Applicants' initial attempts to separate the valuable 4-acetoxystyrene from the multi-component mixture with the help of other, less thermally destructive methods, such as extraction, supercritical extraction, or adsorption, failed because it was not possible to find a sufficiently selective extraction or adsorption agent.

SUMMARY OF THE INVENTION

In accordance with the present invention, it has been discovered that even in instances when there are a large number of impurities present in a crude product 4-acetoxystyrene, a high degree of purification with good yields can be attained by subjecting the crude product mixture to a one-step or multistep melt crystallization process.

The present invention relates, therefore, to a process for the purification of 4-acetoxystyrene from a crude product mixture containing 4-acetoxystyrene, characterized in that the mixture is subjected to a melt crystallization process having at least one crystallization step wherein the final crystallization temperature ranges from about $-50°$ C. to about $+8°$ C.

The starting crude product mixture normally contains at least 50% by weight, preferably 80–95% by weight, calculated on the mixture, of 4-acetoxystyrene. In principle, its content may, however, be lower than 50% by weight 4-acetoxystyrene, for example 40% by weight or even 30% by weight. This crude product mixture generally contains at least 5, and normally 5 to 10 contaminants, such as, but not limited to acetic acid, ethyl benzene, 1-phenyl ethanol, 4-ethyl phenol, 4-hydroxystyrene, 4-ethylphenyl acetate, 4-acetoxyacetophenone, 1-(4-acetoxyphenyl)-ethane, heavy ends and water.

The crystallization temperature(s) used in the process according to the present invention are generally in the range of about $-50°$ to $+8°$ C., preferably between $-35°$ and $+7.8°$ C. The use of seeding crystals is advisable, to initiate crystallization more rapidly, especially in mixtures with less than about 70% by weight of 4-acetoxystyrene. The most favorable temperatures for the initiation of crystallization and the most favorable crystallization times can readily be determined by minimal experimentation. After crystallization of a part (first portion) of the liquid crude product 4-acetoxystyrene, the remaining liquid fraction is rapidly removed. The resulting crystallized first portion comprising 4-acetoxystyrene (which is already more pure) and impurities, mainly in liquid form, which impurities adhere to and are included within the 4-acetoxystyrene crystals and crystal aggregations, respectively, is then slowly heated to separate such impurities upon remelting of part of the crystallized first portion. The liquid runoff generated upon remelting is then removed and the remaining crystallized product (second portion) comprising 4-acetoxystyrene may be used as it is or subsequently remelted and subjected, preferably at least once more, to further melt crystallization in a manner analogous to that previously described, until the requisite degree of purity is reached.

Typically adequate purity of the 4-acetoxystyrene is achieved after one to five, preferably two or three, melt crystallization cycles. The non-crystallized liquid fractions obtained during the crystallization steps, and which still contain 4-acetoxystyrene can be repeatedly subjected to renewed melt crystallization either as part of a recycle stream or independently. In theory, continued purification via melt crystallization is possible until the eutectic composition is reached in the liquid fraction. For practical purposes, melt crystallization processing will be discontinued a few percent above this eutectic composition.

Due to the large number of contaminants present in the starting crude product mixture comprising 4-acetoxystyrene, it is necessary to control carefully the cooling rate during the crystallization step and the heating rate during a remelting step used to separate (expell) impurities included within the crystal aggregations. The cooling rate of the crude product mixture (initially or during subsequent recrystallizations) below the freezing point of the mixture should typically range from about 0.005° C./min to about 0.1° C./min, and preferably from about 0.01° C./min to about 0.08° C./min. The heating rate for the remelting, impurity expulsion step, should range from about 0.005° C./min to about 0.08° C./min, and preferably from 0.01° C./min to about 0.06° C./min.

DETAILED DESCRIPTION OF THE INVENTION

According to one embodiment of the invention, which embodiment is normally carried out batchwise, the liquid crude product mixture in the first crystallization step is initially cooled to a temperature typically ranging from about 0.1° C. to about 5° C. below the freezing point of the mixture. Preferably the first crystallization step is carried out to a temperature ranging from about 1° C. to about 4° C. below the freezing point of the mixture, wherein the mixture is seeded, typically with 4-acetoxystyrene seed crystals (in any case, the mixture temperature must be lower than the freezing point of the seed crystals or the seed crystals will melt), and then the mixture is maintained at that temperature for some time, normally about 0.1 to about 1 hour, preferably about 0.4 to about 0.8 hour. Thereafter, the mixture is further cooled at a rate of 0.005° C./min to 0.1° C./min, preferably at a rate of 0.01° C./min to 0.08° C./min, to the lowest crystallization temperature. The lowest crystallization temperature in the first crystallization step, depending on the kind and amount of the impurities present in the crude product mixture, is typically between about +7.8° C. and about −35° C., and preferably between about 0° C. and about −35° C. In case of crude product mixtures having a very low content of 4acetoxystyrene, the lowest crystallization temperature may be even lower. The liquid fraction is drained off, after the mixture reaches the final crystallization temperature.

To accomplish additional purification, the temperature of the remaining crystallized portion of the mixture is then slowly raised, at a rate of generally about 0.005° C./min to about 0.08° C./min, preferably, at a rate of about 0.01° C./min to about 0.06° C./min, to separate the impurities adhering to the exterior of the crystallized 4-acetoxystyrene or included within the 4-acetoxystyrene crystal aggregations. The temperature of the remaining crystallized 4-acetoxystyrene is increased until the freezing point of the melted, liquid runoff is between about −20° C. and about +5° C., preferably between −20° C. and 4° C. In this way several contaminated liquid fractions are obtained. The solid 4-acetoxystyrene product remaining after removal of the contaminated liquid fractions can then be melted, and subjected to the next crystallization step.

The crystallization and heating temperatures of each successive melt crystallization cycle are higher, in accordance with the higher degree of purity of the 4-acetoxystyrene. Typically, the temperature ranges over which crystallization and heating are carried out are narrower ranges as the 4-acetoxystyrene content of the feed mixture increases (higher degree of purity).

Typically three, and as many as six, liquid fractions can be obtained, during the heating to separate impurities, within the respective melt crystallization cycles; each liquid fraction exhibits a different degree of purity of 4-acetoxystyrene. The first fraction, obtained at the lowest temperature, is the most highly contaminated, followed by fraction 2, which is followed in turn by fraction 3 and so on to the final fraction, obtained at the highest melted liquid fraction runoff temperature, which final fraction exhibits the least contamination. Some of the fractions can be combined with fresh crude product for the next crystallization process while other fractions are preferably subjected to an independent clean-up by melt crystallization, depending on their degree of purity.

The liquid fractions processed by independent melt crystallization clean-up contain very low contents of 4-acetoxystyrene, for example 50% by weight or even less. However, even such low purity 4-acetoxystyrene, which requires the use of very low crystallization temperatures (causing an increase in the viscosity of the melt and thereby reducing crystallization speed), can be further purified at a relatively high speed using the melt crystallization process, and provides 4-acetoxystyrene in surprisingly high yields at high purities. The liquid fractions processed by independent melt crystallization for clean up purposes can be fed back into the first crystallization step for the crude product 4acetoxystyrene, thus increasing considerably the overall yield of the process.

The residual 4-acetoxystyrene which is too contaminated to be fed back into the crude product feed can be recovered by distillation.

In principle, the process according to the present invention can be carried out in any closed crystallizer which enables melt crystallization; the melt crystallization is preferably multistep and takes place in rapid sequence, preferably under inert gas and with exclusion of moisture. Suitable for this purpose is, for example, a tube crystallizer (called a drip apparatus) as is described in Winnacker-Kuchler, Chemische Technologie (Chemical Technology), 4th edition, Vol. 6 (1982), page 148, and which is operated discontinuously. A crystallizer as described in U.S. Pat. No. 3,621,664, which allows the process to be carried out semicontinuously, can be also used to practice the present invention.

The 4-acetoxystyrene purified according to the present invention generally has a purity of more than 99%, by weight. Typically the purity ranges from about 99.3% by weight to about 99.9% by weight, even after a few crystallization steps.

It is surprising that the melt crystallization of the 4-acetoxystyrene crude product mixture, which is a highly empiric purification method, being influenced by a large number of parameters, including seed formation, crystal growth rate, type of crystals, viscosity of the melt, molecular weight and kind of impurities, etc. (see Chem.-Ing.-Techn. 57, (1985), No. 2, pages 91–102) would lead to such high degrees of purity after a few crystallization steps. This is particularly true due to the large number and amount of impurities in the crude product mixture, and the low crystallization temperatures required in view of these factors. Further, it was unexpected that crystallization temperatures as low as −25° C. or lower cause no isolated subcooling, which subcooling can considerably delay or even prevent melt crystallization.

The process of the present invention is illustrated in the following examples, which examples are for purposes of enabling one skilled in the art to practice the present invention but are not intended to be limitations upon the scope of the invention.

EXAMPLES

Example 1

A 4-acetoxystyrene crude product mixture having a freezing point of 3.8° C. was placed in a tube crystallizer as is described in Winnacker-Kuchler, Chemische Technologie (Chemical Technology), 4th edition, Vol. 6 (1982), page 148. However, instead of a bundle of tubes the apparatus used contained only a single vertical tube about 1.46 inches in diameter which tube crystallizer was heated and cooled using a jacket on the exterior wall of the tube. The jacket was equipped with a thermostat having a time-temperature regulator. The crude liquid mixture comprising 4-acetoxystyrene was pumped into the tube until the tube was completely filled with it.

The analyzed composition of the 4-acetoxystyrene crude product mixture was as follows:

| | |
|---|---|
| 4-acetoxystyrene (4-ASM) | 95.00% |
| 4-Acetoxyphenylmethyl carbinol | 0.80% |
| Acetic acid | 0.90% |
| Ethyl benzene | 0.02% |
| 1-Phenyl ethanol | 0.16% |
| 4-Ethyl phenol | 1.00% |
| 4-Hydroxystyrene | 0.30% |
| 4-Ethylphenyl acetate | 1.40% |
| 4-Acetoxyacetophenone | 0.30% |
| 1-(4-Acetoxyphenyl)-ethane | 0.08% |
| Heavy ends | — |
| Water | 0.45% |

The liquid mixture was cooled to +1.0° C. and the cooled mixture was then seeded with a few seed crystals of 4-acetoxystyrene.

After a crystallization processing time of half an hour at +1 0° C., the crystallizer contents were further cooled, over a time period of about 5 ½ hours, to −11.7° C. The liquid remaining in the crystallizer apparatus was then drained off, leaving a crystallized portion of the crude mixture within the whole tube. The temperature inside the apparatus was then slowly increased until the freezing point of the runoff from the contents of the tube crystallizer was 3.3° C. The colorless crystals retained in the apparatus were then melted and the melt was isolated. The liquid 4-acetoxystyrene mixture obtained, which had a freezing point of 7.1° C., was then cooled using the crystallizer apparatus to 4.9° C., and seeded with a few crystals as previously described. After a crystallizing time at 4.9° C. of half an hour, the mixture was further cooled to 0° C. over a time period of about 4 ½ hours. The liquid portion of mixture remaining in the apparatus was drained off and the temperature of the remaining apparatus contents was slowly raised until the freezing point of the runoff was 4.2° C. Again, the crystals remaining in the tube crystallizer were melted and the melt was isolated.

The contaminated fractions of the mixture obtained as runoff were further processed subsequently, as described in Examples 4 and 5 below. Thus, it was discovered that using a starting crude product of 114.5 parts by weight, 100 parts by weight of purified 4-acetoxystyrene were produced. The overall yield, including the amounts of 4-acetoxystyrene obtained by subsequent processing as described in Examples 4 and 5 (calculated on the basis of a Sankey diagram), was 87.3%. The pure 4-acetoxystyrene product had a freezing point of 7.8° C. and a purity of 99.9%.

Example 2

The same crude product mixture used in Example 1 and the same apparatus were used in this example. The liquid mixture was cooled to +1.0° C. and seeded with a few seed crystals of 4-acetoxystyrene. After a crystallization processing time of about half an hour at −1.1° C., the crystallizer contents were further cooled over a time period of about 6 hours to −13.1° C. The liquid remaining in the crystallization apparatus was then drained off and the temperature inside the apparatus was slowly increased until the freezing point of the runoff from the tube crystallizer was 2.9° C. The colorless crystals retained in the apparatus were then melted and the melt was isolated.

The isolated melted 4-acetoxystyrene mixture obtained, which had a freezing point of 6.7° C., was then cooled using the crystallizer apparatus to 4.0° C., and seeded with a few crystals of 4-acetoxystyrene. After a crystallizing time of three quarters of an hour at 4.0° C., the mixture was further cooled to −5.0° C. over a time period of about 6 ½ hours. The liquid portion of the mixture remaining was then drained off and the temperature of the remaining apparatus contents was slowly raised until the freezing point of the runoff from the tube crystallizer was 5.4° C. Again, the crystals remaining in the apparatus were melted and the melt was isolated. The contaminated fractions of the mixture obtained as runoff were further processed subsequently, as described in Examples 4 and 5 below.

Thus, it was discovered that using a starting crude product of 113.3 parts by weight, 100 parts by weight of purified 4-acetoxystyrene was produced. The overall yield, including again (as in Example 1) the amounts of 4-acetoxystyrene obtained by subsequent processing as described in Examples 4 and 5, and calculated on the basis of a Sankey diagram, was 88.3%. The pure 4-acetoxystyrene product had a freezing point of 7.6° C. and a purity of 99.5%.

Example 3

A 4-acetoxystyrene-comprising mixture having a freezing point of −0.3° C., was placed in the tube crystallizer of Example 1.

The analyzed composition of the 4-acetoxystyrene crude product mixture was as follows:

| | |
|---|---|
| 4-acetoxystyrene (4-ASM) | 88.50% |
| 4-Acetoxyphenylmethyl carbinol | 4.57% |
| Acetic acid | 0.75% |
| Ethyl benzene | 0.03% |
| 1-Phenyl ethanol | 0.15% |
| 4-Ethyl phenol | 0.75% |
| 4-Hydroxystyrene | 0.45% |
| 4-Ethylphenyl acetate | 1.00% |
| 4-Acetoxyacetophenone | 1.42% |
| 1-(4-Acetoxyphenyl)-ethane | 0.75% |
| Hevy ends | 0.60% |
| Water | 0.97% |

The liquid mixture was cooled to −2.1° C. and then seeded with a few seed crystals of 4-acetoxystyrene. After a crystallization processing time of about half an hour at −2.1° C., the crystallizer contents were cooled, over a time period of about 5 ½ hours, to −12.7° C. The liquid remaining in the crystallizer apparatus was then drained off and the temperature inside the apparatus was slowly increased until the freezing point of the runoff from the contents of the apparatus was −1.3° C. The colorless crystals retained in the apparatus were then melted and the melt was isolated. The 4-acetoxystyrene melted mixture obtained, which had a freezing point of had a freezing point of 5.4° C., was then cooled using the crystallizer to 3.0° C. and seeded with a few crystals as previously described. After a crystallizing time at 3.0° C. of half an hour, the mixture was further cooled to −4.7° C. over a time period of about 4 ¼ hours. The liquid portion of mixture remaining in the apparatus was drained off and the temperature of the remaining apparatus contents was slowly raised until the freezing point of the runoff was 3.4° C. Again, the crystals remaining in the apparatus were melted and the melt was isolated. The 4-acetoxystyrene melted mixture obtained had a freezing point of 6.6° C. The isolated mixture was further purified using the techniques of the kind described above. The isolated mixture was cooled to 4.0° C., then seeded, and after half an hour at 4.0° C., was cooled to 0.1° C. over a time period of about 4 ½ hours. The liquid mixture remaining was drained off and the temperature inside the apparatus was slowly increased until the freezing point of the runoff was 3.9° C. The crystals in the apparatus were then melted and isolated. The contaminated fractions obtained as runoff were further processed subsequently, as described in Examples 4 and 5 below. Thus, it was discovered that using a starting crude product mixture of 132.7 parts by weight, 100 parts by weight of purified 4-acetoxystyrene was produced. The overall yield, including the amount of 4-acetoxystyrene obtained by subsequent processing as described in Examples 4 and 5, and calculated on the basis of a Sankey diagram, was 75.6%. The pure 4-acetoxystyrene product had a freezing point of 7.1° C. and a purity of 99.3%.

Example 4

A 4-acetoxystyrene-comprising mixture having a freezing point of 1.2° C. and a purity of 89.6% was placed in the crystallizing apparatus previously described in Example 1 and was processed using the techniques described therein. The liquid mixture was cooled to −1.1° C. and seeded with a few seed crystals of 4-acetoxystyrene. After a crystallization time at −1.1° C. of about half an hour, the crystallizer contents were cooled, over a time period of about 6 ¼ hours, to −14.7° C. The liquid portion of the mixture remaining in the crystallization apparatus was then drained off and the temperature of the remaining crystalline contents was slowly raised until the freezing point of the runoff was −3.7° C. The colorless crystals retained in the tube crystallizer were melted and the melt was isolated. For every 120.2 parts by weight of starting material, 100 parts by weight of purified 4-acetoxystyrene was obtained; the yield was 83.2%. The isolated product had a freezing point of 5.5° C. and a purity of 95.2%. Subsequently, the product from this Example was subjected to further purification in combination with the isolated product mixture obtained in Example 5.

Example 5

A 4-acetoxystyrene-comprising mixture having a freezing point of −12.2° C. and a purity of 65.1% was placed in the tube crystallizer of Example 1. The liquid mixture was cooled to −14.0° C. and seeded with a few seed crystals. After a crystallization processing time of about half an hour at −14.0° C., the crystallizer contents were further cooled, over a time period of about 5 ¼ hours, to −29.5° C. The liquid portion of the mixture remaining in the apparatus was then drained off and the temperature of the remaining apparatus contents was slowly raised until the freezing point of the runoff from the tube crystallizer was −17.8° C. The colorless crystals retained in the apparatus were melted and the melt was isolated. For every 222.0 parts by weight of starting material, 100 parts by weight of purified 4-acetoxystyrene was obtained; the yield was 45%. The isolated product comprising 4-acetoxystyrene had a freezing point of −1.4° C. and a purity of 88.3%. Subsequently, the product from this Example was subjected to further purification in combination with the isolated product mixture obtained in Example 4.

While specific process conditions and process apparatus are described in the preferred embodiments above, to enable one skilled in the art to practice the invention, one skilled in the art will also be able to make modifications and adjustments which are obvious extensions of the present invention. Such obvious extensions of or equivalents to the present invention are intended to fall within the scope of the present invention, as demonstrated by the claims which follow.

What we claim is:

1. A process for purifying 4-acetoxystyrene from a crude mixture comprising 4-acetoxystyrene by melt crystallization, the process comprising the steps of:
   a) cooling a crude liquid mixture comprising 4-acetoxystyrene to a temperature ranging from about +8° C. to about −50° C., whereby a first portion of the mixture is crystallized;
   b) removing at least substantial amounts of the liquid mixture remaining after step a); and
   c) subsequently slowly heating the crystallized first portion while simultaneously removing liquid which forms due to the heating, whereby impurities contained in the liquid which forms are removed from the crystallized first portion, producing a crystallized second portion.

2. The process of claim 1 including an additional step:
   d) melting the crystallized second portion, whereby a purified liquid comprising 4-acetoxystyrene is obtained.

3. The process of claim 2, wherein steps a) through d) are repeated at least once, using the melt from said crystallized second portion as said crude liquid mixture in step a).

4. The process of claim 3, wherein step d) is repeated between one and four times, and a) through c) are carried out between two and five times.

5. The process of claim 1, claim 2, claim 3, or claim 4 wherein the crude mixture contains at least 50% by weight of 4-acetoxystyrene.

6. The process of claim 5, wherein the crude mixture contains at least 80% by weight of 4-acetoxystyrene.

7. The process of claim 5, wherein the crude mixture comprising 4-acetoxystyrene contains substantial amounts of at least 5 other substances.

8. The process of claim 5, wherein the crystallization temperature ranges from about −35° C. to about +8.0° C.

9. A process for purifying 4-acetoxystyrene from a crude mixture comprising 4-acetoxystyrene by melt crystallization, the process comprising the steps of:
 a) cooling a crude mixture comprising 4-acetoxystyrene to a temperature ranging from about 1° C. to about 4° C. below the freezing point of the crude mixture;
 b) seeding the cooled mixture of step a) with seed crystals;
 c) cooling the seeded mixture of step b) to a temperature at least 2° C. below the freezing temperature of the crude mixture, for a period of time sufficient to permit substantially complete crystallization of the seeded mixture at that temperature, whereby a crystallized first portion mixture is obtained;
 d) removing the liquid mixture remaining after step c);
 e) subsequently slowly heating the crystallized first portion while simultaneously removing liquid which forms due to the heating, whereby impurities contained in the liquid which forms are removed from the crystallized first portion, producing a crystallized second portion.

10. The process of claim 9, including an additional step
 f) melting the crystallized second portion, whereby a purified liquid comprising 4-acetoxystyrene is obtained.

11. The process of claim 10, wherein steps a) through f) are repeated at least once, using the melt from said crystallized second portion as said crude liquid mixture to step a).

12. The process of claim 9, claim 10, or claim 11, wherein the step a) cooling of the crude mixture from the freezing point to the temperature ranging from about 1° C. to about 4° C. below the freezing point is carried out at a rate ranging from about 0.01° C./min to about 0.08° C./min.

13. The process of claim 9, claim 10, or claim 11, wherein the step e) heating of the crystallized first portion is carried out by raising the temperature of at least part of the first portion at a rate ranging from about 0.01° C./min to about 0.08° C./min.

14. The process of claim 9 wherein the liquid from step e) is combined with the crude mixture of step a).

15. The process of claim 9, wherein the liquid from step e) is isolated and subsequently further purified by:
 a) cooling a crude mixture comprising 4-acetoxystyrene to a temperature ranging from about 1° C. to about 4° C. below the freezing point of the crude mixture;
 b) seeding the cooled mixture of step a) with seed crystals;
 c) cooling the seeded mixture of step b) to a temperature at least 2° C. below the freezing temperature of the crude mixture, for a period of time sufficient to permit substantially complete crystallization of the seeded mixture at that temperature, whereby a crystallized first portion mixture is obtained;
 d) removing the liquid mixture remaining after step c); and
 e) subsequently slowly heating the crystallized first portion while simultaneously removing liquid which forms due to the heating,
whereby impurities contained in the liquid which forms are removed from the crystallized first portion, producing a crystallized second portion.

16. The process of claim 9, wherein the liquid from step e) is isolated and subsequently further purified by:
 a) cooling a crude mixture comprising 4-acetoxystyrene to a temperature ranging from about 1° C. to about 4° C. below the freezing point of the crude mixture;
 b) seeding the cooled mixture of step a) with seed crystals;
 c) cooling the seeded mixture of step b) to a temperature at least 2° C. below the freezing temperature of the crude mixture, for a period of time sufficient to permit substantially complete crystallization of the seeded mixture at that temperature, whereby a crystallized first portion mixture is obtained;
 d) removing the liquid mixture remaining after step c);
 e) subsequently slowly heating the crystallized first portion while simultaneously removing liquid which forms due to the heating, whereby impurities contained in the liquid which forms are removed from the crystallized first portion, producing a crystallized second portion; and
 f) melting the crystallized second portion,
whereby a purified liquid comprising 4-acetoxystyrene is obtained.

17. The process of claim 9, wherein the liquid from step e) is isolated and subsequently further purified by:
 a) cooling a crude mixture comprising 4-acetoxystyrene to a temperature ranging from about 1° C. to about 4° C. below the freezing point of the crude mixture;
 b) seeding the cooled mixture of step a) with seed crystals;
 c) cooling the seeded mixture of step b) to a temperature at least 2° C. below the freezing temperature of the crude mixture, for a period of time sufficient to permit substantially complete crystallization of the seeded mixture at that temperature, whereby a crystallized first portion mixture is obtained;
 d) removing the liquid mixture remaining after step c);
 e) subsequently slowly heating the crystallized first portion while simultaneously removing liquid which forms due to the heating, whereby impurities contained in the liquid which forms are removed from the crystallized first portion, producing a crystallized second portion;
 f) melting the crystallized second portion; and
 g) repeating steps a) through e) at least once,
whereby a purified liquid comprising 4-acetoxystyrene is obtained.

18. The process of claim 9, wherein the liquid from step e) is combined with the liquid mixture removed in step d) and is subsequently further purified by:
 a) cooling a crude mixture comprising 4-acetoxystyrene to a temperature ranging from about 1° C. to about 4° C. below the freezing point of the crude mixture;
 b) seeding the cooled mixture of step a) with seed crystals;
 c) cooling the seeded mixture of step b) to a temperature at least 2° C. below the freezing temperature of the crude mixture, for a period of time sufficient to permit substantially complete crystallization of the seeded mixture at that temperature, whereby a crystallized first portion mixture is obtained;
 d) removing the liquid mixture remaining after step c); and e) subsequently slowly heating the crystallized first portion while simultaneously removing liquid which forms due to the heating, whereby impurities contained in the liquid which forms are removed from the crystallized first portion, producing a crystallized second portion.

19. The process of claim 9, wherein the liquid from step e) is combined with the liquid mixture removed in step d) and is subsequently further purified by:

a) cooling a crude mixture comprising 4-acetoxystyrene to a temperature ranging from about 1° C. to about 4° C. below the freezing point of the crude mixture;

b) seeding the cooled mixture of step a) with seed crystals;

c) cooling the seeded mixture of step b) to a temperature at least 2° C. below the freezing temperature of the crude mixture, for a period of time sufficient to permit substantially complete crystallization of the seeded mixture at that temperature, whereby a crystallized first portion mixture is obtained;

d) removing the liquid mixture remaining after step c);

e) subsequently slowly heating the crystallized first portion while simultaneously removing liquid which forms due to the heating, whereby impurities contained in the liquid which forms are removed from the crystallized first portion, producing a crystallized second portion; and f) melting the crystallized second portion, whereby a purified liquid comprising 4-acetoxystyrene is obtained.

20. The process of claim 9, wherein the liquid from step e) is combined with the liquid mixture removed in step d) and is subsequently further purified by:

a) cooling a crude mixture comprising 4-acetoxystyrene to a temperature ranging from about 1° C. to about 4° C. below the freezing point of the crude mixture;

b) seeding the cooled mixture of step a) with seed crystals;

c) cooling the seeded mixture of step b) to a temperature at least 2° C. below the freezing temperature of the crude mixture, for a period of time sufficient to permit substantially complete crystallization of the seeded mixture at that temperature, whereby a crystallized first portion mixture is obtained;

d) removing the liquid mixture remaining after step c);

e) subsequently slowly heating the crystallized first portion while simultaneously removing liquid which forms due to the heating, whereby impurities contained in the liquid which forms are removed from the crystallized first portion, producing a crystallized second portion;

f) melting the crystallized second portion; and g) repeating steps a) through e) at least once, whereby a purified liquid comprising 4-acetoxystyrene is obtained.

21. The process of claim 1, wherein steps a) through c) are repeated at least once, using the melt from said crystallized first portion as said crude liquid mixture to step a).

22. The process of claim 9, wherein steps a) through e) are repeated at least once, using the melt from said crystallized first portion as said crude liquid mixture to step a).

23. The process of claim 22, wherein the steps a) cooling of the crude mixture from the freezing point to the temperature ranging from about 1° C. to about 4° C. below the freezing point is carried out at a rate ranging rom about 0.01° C./min to about 0.08° C./min.

24. The process of claim 22, wherein the step e) heating of the crystallized first portion is carried out by raising the temperature of at least part of the first portion at a rate ranging from about 0.01° C./min to about 0.08° C./min.

* * * * *